United States Patent
Wan et al.

(10) Patent No.: US 9,029,099 B2
(45) Date of Patent: May 12, 2015

(54) FIBROUS STRUCTURE

(71) Applicant: Agency for Science, Technology and Research, Singapore (SG)

(72) Inventors: Andrew Chwee Aun Wan, Singapore (SG); Tze Chiun Lim, Singapore (SG); Meng Fatt Leong, Singapore (SG); Jackie Y. Ying, Singapore (SG); Jerry Kah Chin Toh, Singapore (SG)

(73) Assignees: Andrew Chwee Aun Wan, Singapore (SG); Tze Chiun Lim, Singapore (SG); Meng Fatt Leong, Singapore (SG); Jackie Y. Ying, Singapore (SG); Jerry Kah Chin Toh, Singapore (SG)

( * ) Notice: Subject to any disclaimer, the term of this patent is extended or adjusted under 35 U.S.C. 154(b) by 0 days.

(21) Appl. No.: 13/867,533

(22) Filed: Apr. 22, 2013

(65) Prior Publication Data

US 2014/0011227 A1    Jan. 9, 2014

Related U.S. Application Data

(63) Continuation of application No. 13/836,722, filed on Mar. 15, 2013, now abandoned.

(30) Foreign Application Priority Data

Mar. 15, 2012  (SG) .................................. 201201899

(51) Int. Cl.
| | | |
|---|---|---|
| A61K 47/36 | (2006.01) | |
| A61K 35/36 | (2006.01) | |
| C12Q 1/02 | (2006.01) | |
| C12N 11/10 | (2006.01) | |
| G01N 33/50 | (2006.01) | |
| C12N 5/071 | (2010.01) | |
| C12N 5/0775 | (2010.01) | |
| A61K 47/26 | (2006.01) | |

(52) U.S. Cl.
CPC ............... *C12Q 1/025* (2013.01); *C12N 11/10* (2013.01); *A61K 35/35* (2013.01); *A61K 47/26* (2013.01); *A61K 35/36* (2013.01); *G01N 33/5088* (2013.01); *C12N 5/0627* (2013.01); *C12N 5/0666* (2013.01); *C12N 2501/12* (2013.01); *C12N 2501/15* (2013.01)

(58) Field of Classification Search
None
See application file for complete search history.

(56) References Cited

U.S. PATENT DOCUMENTS 7,597,885 B2 *  10/2009  Barrows et al. .............. 424/93.7

FOREIGN PATENT DOCUMENTS

WO    WO 2007/109223    *  9/2007   ............... C12N 5/06
WO    WO 2011/102803    *  8/2011   ............... A61L 27/26

OTHER PUBLICATIONS

Yim et al, Biomaterials, 2006, pp. 6111-6122.*

* cited by examiner

*Primary Examiner* — Allison Fox
(74) *Attorney, Agent, or Firm* — Conley Rose, P.C.

(57) ABSTRACT

A fibrous structure comprising an assembly of hair follicle cells within a fibrous matrix.

14 Claims, 5 Drawing Sheets

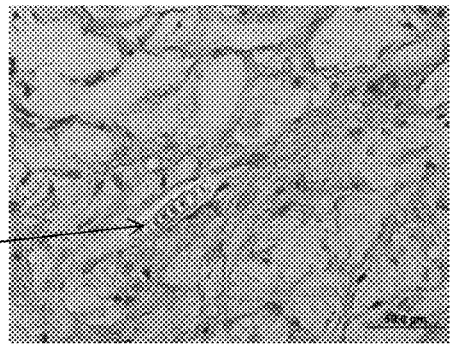 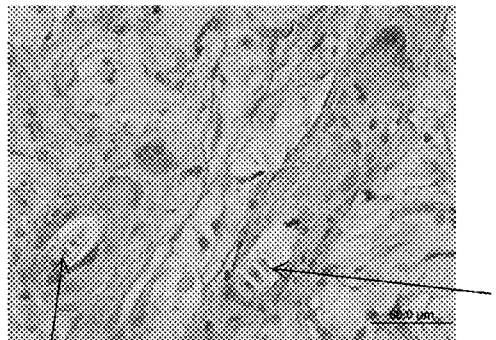
Fig. 3a    Fig. 3b
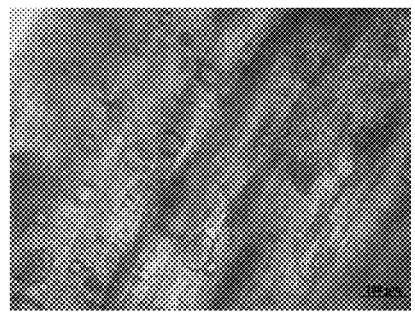 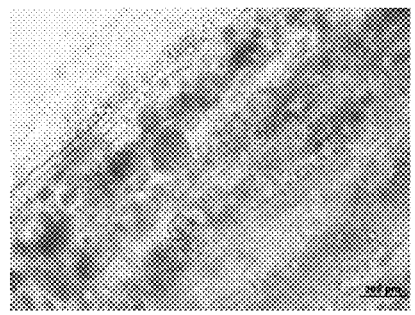
Fig. 4a    Fig. 4b
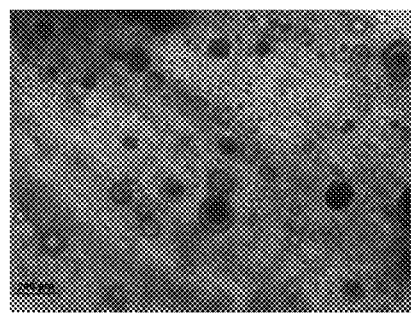 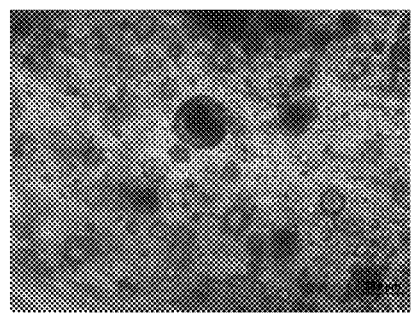
Fig. 4c    Fig. 4d

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: Artificial Versican primer sequence
```

<400> SEQUENCE: 1
ccagcaagca caaaatttca                                                    20

<210> SEQ ID NO 2
<211> LENGTH: 21
<212> TYPE: DNA
<213> ORGANISM: Artificial
<220> FEATURE:
<223> OTHER INFORMATION: Artificial Versican primer sequence

<400> SEQUENCE: 2
tgcactggat ctgtttcttc a                                                  21

<210> SEQ ID NO 3
<211> LENGTH: 20
<212> TYPE: DNA
<213> ORGANISM: Artificial
<220> FEATURE:
<223> OTHER INFORMATION: Artificial BMP4 primer sequence

<400> SEQUENCE: 3
tccacagcac tggtcttgag                                                    20

<210> SEQ ID NO 4
<211> LENGTH: 22
<212> TYPE: DNA
<213> ORGANISM: artificial
<220> FEATURE:
<223> OTHER INFORMATION: Artificial BMP4 primer sequence

<400> SEQUENCE: 4
gggatgttct ccagatgttc tt                                                 22

<210> SEQ ID NO 5
<211> LENGTH: 20
<212> TYPE: DNA
<213> ORGANISM: Artificial
<220> FEATURE:
<223> OTHER INFORMATION: Artificial Nexin1 primer sequence

<400> SEQUENCE: 5
gcgtaaatgg agttggtaaa                                                    20

<210> SEQ ID NO 6
<211> LENGTH: 20
<212> TYPE: DNA
<213> ORGANISM: Artificial
<220> FEATURE:
<223> OTHER INFORMATION: Artificial Nexin1 primer sequence

<400> SEQUENCE: 6
gtctatggtc ttggtgctga                                                    20

<210> SEQ ID NO 7
<211> LENGTH: 23
<212> TYPE: DNA
<213> ORGANISM: Artificial
<220> FEATURE:
<223> OTHER INFORMATION: Artificial IGF1 primer sequence

<400> SEQUENCE: 7
cctcctcgca tctcttctac ctg                                                23

<210> SEQ ID NO 8

```
<211> LENGTH: 21
<212> TYPE: DNA
<213> ORGANISM: Artificial
<220> FEATURE:
<223> OTHER INFORMATION: Artificial IGF1 primer sequence

<400> SEQUENCE: 8
ctgctggagc cataccctgt g                                              21

<210> SEQ ID NO 9
<211> LENGTH: 20
<212> TYPE: DNA
<213> ORGANISM: Artificial
<220> FEATURE:
<223> OTHER INFORMATION: Artificial SCF primer sequence

<400> SEQUENCE: 9
ccattgatgc cttcaaggac                                                20

<210> SEQ ID NO 10
<211> LENGTH: 20
<212> TYPE: DNA
<213> ORGANISM: Artificial
<220> FEATURE:
<223> OTHER INFORMATION: Artificial SCF primer sequence

<400> SEQUENCE: 10
ggctgtctct tcttccagta                                                20
```

FIBROUS STRUCTURE

CROSS-REFERENCE TO RELATED APPLICATIONS

This application is a continuation of, and claims the benefit of, application Ser. No. 13/836,722 filed Mar. 15, 2013, entitled "A FIBROUS STRUCTURE", which claims priority to Singapore application number SG 201201899-0 filed Mar. 15, 2012, which is hereby incorporated by reference in its entirety.

STATEMENT REGARDING FEDERALLY SPONSORED RESEARCH OR DEVELOPMENT

Not applicable.

TECHNICAL FIELD

The present invention generally relates to a fibrous structure. The present invention also relates to a method of forming the fibrous structure.

BACKGROUND

The issue of hair growth or hair loss disorders has persistently bothered men, women and children of all ages. There are various reasons as to the causes of such disorders including aging, diseases and medical treatments. To address the various causes of hair disorders, several solutions for the reduction of hair loss and stimulation of hair growth are available depending on the causes in each individual's case. Some of these solutions may include dietary supplements, pharmaceutical drugs or even hair transplantation. The drawbacks to some of these solutions are the occurrence of side effects or that their effects fall short of the ultimate goal of mitigating hair disorders, e.g., minoxidil tends to produce fine hairs instead of mature hairs; finasteride tends to slow down baldness instead of promoting hair growth. Hence, there is a need for more and better drugs for the targeted treatment of hair disorders.

To create new drugs, various bioengineered scaffolds have been constructed to mimic the cellular structure of the scalp or other parts of the body, in particular the epithelial-mesenchymal interactions in the hair follicle (HF), for pre-clinical assessment of these new drugs.

Previous efforts include creating a layered scaffold that comprises of a pseudodermis (a collagen base mixed with human dermal fibroblasts (HDF)). Later, these pseudodermis may be covered with various cells and matrix mixtures which contained basement membranes and extracellular components. For example, covering with a first layer containing Matrigel™ mixed with dermal papilla fibroblasts (DPC) on top of the pseudodermis followed by another layer containing outer root sheath keratinocytes (ORSK).

Another similar construct known as the mixed layered system comprises of covering the pseudodermis with a single matrix containing Matrigel™, DPC and ORSK rather than having them in separate layers.

The problem with such layered scaffolds is that they have to be subjected to histochemical stainings for accurate analysis. It is also known that the construction of such layered structures, which are very laborious and time consuming resulting in low throughput, tend to result in disappointing structural appearances that do not mimic actual hair follicles intended for use in pre-clinical investigations.

One other technique may involve seeding the cell mixture onto membranes where the cells are able to aggregate, proliferate, or differentiate and eventually detach off the membranes. Spheroid constructs with a mixture of dermal papilla and ORSK have also been fabricated by extruding the cells (mixed with collagen) into a gelling bath. Likewise, both of these methods and construct configurations suffer from the abovementioned issues, in particular lacking the HF architecture and proper orientation of DPC and keratinocytes. Moreover, these structures cannot be easily analyzed due to the need for fixation, to be sectioned and histochemically stained before visualizations of the structures are enabled.

Accordingly, there is a need for engineered scaffolds constructed in a manner such that it allows for the epithelial-mesenchymal interactions, encourage cell proliferation and prevent apoptosis.

Accordingly, there is a need for a method of constructing said engineered scaffolds that is less labor intensive and easily reproducible to achieve higher throughput.

There is a need to provide a testing platform for drugs used in hair treatment that overcomes, or at least ameliorates, one or more of the disadvantages described above.

SUMMARY

According to a first aspect, there is provided a fibrous structure comprising an assembly of hair follicle cells within a fibrous matrix.

The fibrous structure may be an elongated structure and hence may be termed as a "thread-like" fibrous structure. The thread-like fibrous structure may be a hair follicle-like fibrous structure.

Advantageously, the fibrous matrix may act as a scaffold to encapsulate and support the assembly of the hair follicle cells. The fibrous matrix may promote the growth of the hair follicle cells. The fibrous matrix may promote the interaction between the various types of hair follicle cells by bringing the hair follicle cells into closer proximity to each other, thus leading to increased biological interaction between the various types of hair follicle cells in order to form the assembly of hair follicle cells.

Advantageously, the fibrous structure may form hair follicles in vivo.

In one embodiment, there is provided a thread-like fibrous structure comprising an assembly of hair follicle cells within a fibrous matrix.

According to a second aspect, there is provided a method of forming a fibrous structure comprising the step of providing an assembly of hair follicle cells within a fibrous matrix.

The method may be easier and faster as compared to prior art methods of forming a "sandwich" system or microspheres.

The method can be reproduced easily, leading to high throughput and consistency in the quality and integrity of the fibers formed.

Advantageously, as the hair follicle cells are capable of self-assembling, it is not necessary for a user to intervene.

According to a third aspect, there is provided a use of the fibrous structure comprising an assembly of hair follicle cells within a fibrous matrix for testing drugs used in hair treatment.

Advantageously, due to the presence of the fibrous matrix which functions to support the hair follicle cells, if there is a need to change a testing medium containing a different type of drug, this can be carried out easily without any substantial loss of the hair follicle cells from the fibrous matrix by simply removing the fibrous structure from the existing medium, washing and then immersing the fibrous structure in a new medium. This is in comparison to the prior art in which the hair follicle cells are freely floating in a medium such that if there is a need to change the testing medium, the cells would have to be first concentrated (for example by using a centrifuge to pellet the cells), carefully removing the existing medium without disturbing the cell pellet, washing the cell pellet to remove any residual medium, centrifuging the cells again to concentrate the cells and then adding the new medium. Hence, savings in time and processing steps can be achieved when using the fibrous structure.

Advantageously, the transparent nature of the fibers making up the fibrous matrix allows for the direct observation of the hair follicle cells present within the fibrous matrix. Hence, changes to the hair follicle cells due to the presence of a drug can be observed easily either by the naked eye or by a suitable microscopy technique.

Advantageously, the hair follicle cells present in the fibrous matrix can be fixed and stained easily, if necessary, with a detection reagent during drug testing. As such, the hair follicle cells can be visually detected easily. This is in comparison to the prior art in which the cells have to be fixed, sectioned and histochemically stained before they can be visualized.

Advantageously, a plurality of fibrous structures can be combined together to form a construct in order to provide a larger population for data collection.

Definitions

The following words and terms used herein shall have the meaning indicated:

The term "fibrous structure" is to be interpreted broadly to refer to a structure which is made up of a plurality of fibers. The fibers can be directionally or randomly arranged to form a matrix (or hereby termed as a fibrous matrix). The fibers present in the fibrous matrix can be attached or fused to each other by physical interaction, chemical interaction or electrostatic interaction.

The term "fiber" then refers to an elongate particulate in which one dimension of the particulate greatly exceeds at least one other dimension (or the other two dimensions) of the particulate. For example, the fiber can have a length that is at least about 2, 3, 4, 5, 6, 7, 8, 9, 10 or more times longer than a shorter cross-sectional dimension.

The term "assembly" is to be interpreted broadly to refer to a collection or aggregation of hair follicle cells encapsulated by or present on the individual fibers making up the fibrous matrix. The assembly may comprise at least two types of hair follicle cells that can self-assemble and biologically interact with each other to mimic the architecture of an actual hair follicle. Hence, the interaction between the at least two types of hair follicle cells may result in a hair follicle like structure that may resemble the configuration or architecture of an actual hair follicle.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a fibrous structure will now be disclosed. The fibrous structure comprises an assembly of hair follicle cells within a fibrous matrix.

The fibrous structure may be in the form of a thread-like structure or a hair follicle like structure. The hair follicle like structure may be a three-dimensional hair follicle like structure. The fibrous structure may be used to form a fibrous mat. The fibrous structure may be incorporated into a skin patch, where the hair follicle-like structures form the germ for the development of new hair follicles in vivo.

The fibrous structure may have a dimension in the range of about 100 μm to about 200 μm, about 120 μm to about 200 μm, about 140 μm to about 200 μm, about 160 μm to about 200 μm, about 180 μm to about 200 μm, about 100 μm to about 120 μm, about 100 μm to about 140 μm, about 100 μm to about 160 μm or about 100 μm to about 180 μm. The above dimension may refer to the diameter of the fibrous structure, which may have a cylindrical shape.

The length of the fibrous structure is not limited and depends on the requirements of the user. The length of the fibrous structure may be determined by the size of the support (such as a well or plate) used to culture the construct.

The fibrous structure may be placed in a culture medium to promote the formation of the hair follicle like structure. The culture medium to be used depends on the hair follicle cells to be cultured and the person skilled in the art would know what culture medium to use.

The hair follicle cells may be selected from the group consisting of human dermal fibroblasts, human dermal papilla fibroblasts, human dermal microvascular endothelial cells, human keratinocytes, human melanocytes, hair follicle dermal papilla cells, human dermal papilla cells, hair follicle outer root sheath cells, normal human epidermal keratinocytes and outer root sheath keratinocytes.

It is to be noted that the types of the hair follicle cells that can be used in the fibrous structure are those that are able to form a hair follicle architecture when present in the fibrous matrix. The fibrous structure may comprise at least two types of hair follicle cells making up the assembly. The at least two types of hair follicle cells may be able to self-assemble and interact with each other in order to mimic the architecture of an actual hair follicle. In addition, higher expressions of genes that are involved in interactions in the native hair follicle have resulted from using at least two types of hair follicle cells as compared to the gene expressions when only one type of hair follicle cells is used.

In one embodiment, the two types of hair follicle cells may be human dermal papilla cells (hDP) and normal human epidermal keratinocytes (NHEK). When placed in a suitable culture medium such as a mixture of dermal papilla medium with keratinocyte medium in a ratio of 1:1, at certain cell concentrations, due to the close proximity between the hDP and NHEK cells, the hDP cells can aggregate to form spheroids with the NHEK at least partially surrounding the hDP aggregates (or spheroids) to form the fibrous structure. The minimum cell concentration of the hDP cells in order to form the spheroids may be at least about 100 million cells/ml while that for the NHEK to at least partially surround the hDP spheroids may be at least about 50 million cells/ml. The proper orientation of the hDP and NHEK cells (in which the NHEK at least partially surround the hDP aggregates) may result in a fibrous structure having a hair follicle architecture such that the fibrous structure can be viewed as being a hair follicle-like structure. Hence, the hDP cells and NHEK may migrate and self-assemble within the fibrous matrix to form the fibrous structure (or hair follicle like structure.

In another embodiment, the two types of hair follicle cells may be hDP cells with outer root sheath cells.

In an embodiment where hDP spheroids are present, the diameter of the spheroids may be in the range of about 80 µm to about 120 µm, about 90 µm to about 120 µm, about 100 µm to about 120 µm, about 110 µm to about 120 µm, about 80 µm to about 90 µm, about 80 µm to about 100 µm or about 80 µm to about 110 µm. The diameter of the spheroids may be about 100 µm. In instances where the hDP cells do not form an actual spheroid, the above diameter may refer to an equivalent diameter of the irregularly-shaped spheroid.

The fibrous structure may comprise a plurality of individual fibers making up the fibrous matrix. The individual fiber may be a polyionic fiber.

The polyionic fiber may comprise at least one polycationic polymer and at least one polyanionic polymer. The at least one polycationic polymer and/or at least one polyanionic polymer may be biocompatible or biodegradable.

The types of polycationic polymer and/or polyanionic polymer are not limited as long as the polycationic polymer and polyanionic polymer can come together to form a fiber. An exemplary polycationic polymer may be chitin, chitosan or methylated collagen. An exemplary polyanionic polymer may be selected from the group consisting of alginate, gellan, heparan sulfate, heparin, acidic keratin, hyaluronic acid, chondroitin sulfate and combinations thereof.

The fibrous structure may be implanted into a living organism to form a hair follicle in vivo.

A plurality of fibrous structures can be combined together to form a construct in order to provide a larger population for data collection. The number of fibrous structures that can be combined to form a construct is not particularly limited and depends on the needs of the user. In one embodiment, about 10, about 20, about 30, about 40, about 50, about 60, or about 70, fibrous structures can be combined to form a construct.

The cell constructs are stable and the cells may be viable for a long period of time. In one embodiment, the cells may be viable for up to two months.

The fibrous structure may be formed in a method which comprises the step of providing an assembly of hair follicle cells within a fibrous matrix.

The method to form the fibrous structure may be carried out using the interfacial polyelectrolyte complexation (IPC) fiber assembly technique.

The providing step may comprise the step of drawing a fiber from the interface between a polyanionic polymer solution and a polycationic polymer solution to form the fibrous matrix, wherein the hair follicle cells are present in at least one of the polycationic polymer solution and polyanionic polymer solution.

The hair follicle cells may be selected from the group consisting of human dermal fibroblasts, human dermal papilla fibroblasts, human dermal microvascular endothelial cells, human keratinocytes, human melanocytes, hair follicle dermal papilla cells, human dermal papilla cells, hair follicle outer root sheath cells, normal human epidermal keratinocytes and outer root sheath keratinocytes.

Two or more types of hair follicle cells may be present in the assembly.

The two or more types of hair follicle cells may be present in at least one of the polycationic polymer solution and the polyanionic polymer solution.

In one embodiment, where two types of hair follicle cells are desired, one type of hair follicle cells may be present in the polycationic solution (or polyanionic solution) while another type of hair follicle cells may be present in the other of the polyanionic solution (or polycationic solution, as the case may be). If additional types of hair follicle cells are desired, the additional types of hair follicle cells may be in an admixture with the above types of hair follicle cells in the respective solution or may be present in a second polycationic solution (or polyanionic solution) as desired.

The two or more types of hair follicle cells may be present in two or more polycationic polymer solutions such that one type of hair follicle cells is present in one polycationic solution. In an embodiment where two polycationic polymer solutions are used, hDP cells may be present in one polycationic polymer solution and NHEKs may be present in the other polycationic polymer solution.

The two or more types of hair follicle cells may be present in two or more polyanionic polymer solutions such that one type of hair follicle cells is present in one polyanionic solution. In an embodiment where two polyanionic polymer solutions are used, hDP cells may be present in one polyanionic polymer solution and NHEKs may be present in the other polyanionic polymer solution.

In another embodiment, the two or more types of hair follicle cells may be present in the same solution, which can either be the polycationic solution or polyanionic solution.

The concentration of each type of hair follicle cells present in at least one of the polycationic polymer solution and the polyanionic polymer solution may be in the range of about 70 to about 110 million cells/ml, about 70 to about 80 million cells/ml, about 70 to about 90 million cells/ml, about 70 to about 100 million cells/ml, about 80 to about 110 million cells/ml, about 90 to about 110 million cells/ml or about 100 to about 110 million cells/ml.

The at least one polycationic polymer and/or at least one polyanionic polymer may be biocompatible or biodegradable.

The types of polycationic polymer and/or polyanionic polymer are not limited as long as the polycationic polymer and polyanionic polymer can come together to form a fiber. An exemplary polycationic polymer may be chitin or chitosan. An exemplary polyanionic polymer may be selected from the group consisting of alginate, gellan, heparan sulfate, heparin, acidic keratin, hyaluronic acid, chondroitin sulfate, methylated collagen combinations thereof.

At a minimum, one polyanionic solution and one polycationic solution are required in order to form the fiber. The number of polyanionic solutions and polycationic solutions that can be used is not limited and depends on the number of interfaces required in order to form the fiber as well as the number of types of hair follicle cells that are to be present in the fibrous structure.

As the fibers are drawn from the interface between the polycationic and polyanionic solutions, the formed fibers may be collected on a collector (such as a 2-pronged fork). The fiber may be drawn into a humidified chamber to protect the hair follicle cells from drying. After the formed fibers reach a desired height (for example, about 5 cm), the collector or base plate may be rotated to allow the fibers to fuse together in order to form the fibrous matrix.

The rotation speed and number of rotational rounds of the base plate is not particularly limited and can be chosen by a skilled person based on the extent of fusing of the fibers required. An exemplary rotation speed of the base plate may be selected from about 3 to about 7 rpm and an exemplary number of rotational rounds may be selected from about 3 to 7 rounds.

The fusing process may be completed by treating the fibrous matrix to form the final construct by dipping the fibrous matrix in a polycationic polymer solution followed by a polyanionic polymer solution. Here, the polycationic polymer solution may be water soluble chitin and the polyanionic polymer solution may be alginate solution.

The resultant fibrous matrix with the hair follicle cells therein may be placed in a suitable culture medium to allow the hair follicle cells to assemble in the fibrous matrix to thereby form the fibrous structure (or hair follicle like structure). The hair follicle cells may self-assemble within the fibrous matrix to form the hair follicle structure. As mentioned above, where hDP and NHEK are used, the hDP cells aggregate to form spheroids while the NHEK surround the hDP aggregates to form a structure that resembles the hair follicle.

The fibrous structure can then be used as a testing platform for drugs that are used in hair treatment. Hence, there is also provided the use of the fibrous structure for testing drugs used in hair treatment. The drugs may be those that have a hair growth promoting or inhibiting effect. Exemplary drugs or active agents may be selected from the group consisting of minoxidil (Rogaine®), finasteride (Propecia®), dutasteride, ketoconazole, spironolactone, flutamide, latanoprost (Xalatan®) or bimatoprost (Latisse®), capsaicin, isoflavone, cyproterone, estrogens, IGF-1, lipid prostaglandin D2 and combinations there.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 3a is an image showing a hematoxylin and eosin stain of an explant at 21 days. FIG. 3b is an image of the same explant as in FIG. 3b but taken at 28 days. The scale bar in both images is 50 µm.

FIG. 4a is a bright field image of the fibrous structure when cultured in the presence of a hair growth promoter while FIG. 4b is a bright field image of the fibrous structure cultured without the hair growth promoter. FIG. 4c is a bright field image of the fibrous structure when cultured in the presence of a transforming growth factor β2 while FIG. 4d is a bright field image of the fibrous structure cultured without the transforming growth factor β2, The scale bar in all of the images is the same at 200 µm.

FIG. 5a is a micrograph image of the fibrous structure when cultured in the presence of a hair growth promoter while FIG. 5c is a micrograph image of the fibrous structure when cultured in the presence of a transforming growth factor β2 while

DETAILED DESCRIPTION OF DRAWINGS

Figure 1A:
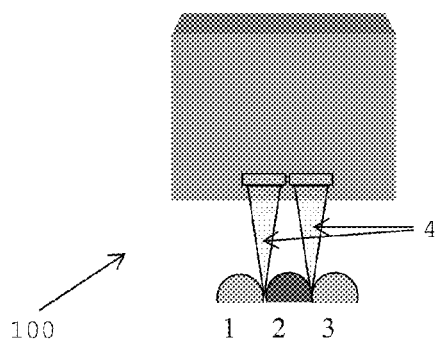
FIG. 1a and FIG. 1b are schematic diagrams showing the set-up of the system used to form a fiber.
Figure 1B:
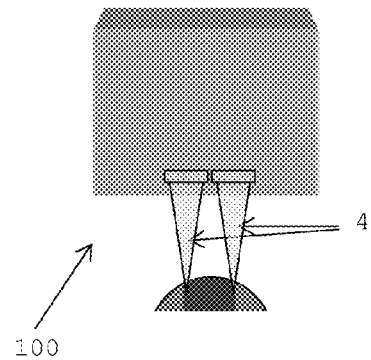

Referring to FIG. 1a and FIG. 1b, there is shown a set-up of a system 100 used to form a fiber.

As shown in FIG. 1a, a polyanionic solution 2 is dispensed between two adhesive modified pipette tips 4 while polycationic solutions (1, 3) are dispensed on the outer opposite sides of the pipette tips. The hair follicle cells can be present in either the polyanionic solution 2 or the polycationic solution (1, 3). Alternatively, the hair follicle cells can be present in only the polycationic solutions (1, 3) such that one type of hair follicle cells is present in one polycationic solution 1 and the other type of hair follicle cells is present in the other polycationic solution 3. It is also possible for the positions of the polyanionic solution 2 and polycationic solutions (1, 3) to be reversed.

Referring to FIG. 1b, the polyanionic solution 2 and polycationic solutions (1, 3) are allowed to come into contact with each other and fibers (not shown) are then drawn by an upward motion of the pipette tips 4 by a motor (not shown).

The fibers are then collected on a collector (not shown) and fused together to form a fibrous structure.

EXAMPLES

Non-limiting examples of the invention will be further described in greater detail by reference to specific Examples, which should not be construed as in any way limiting the scope of the invention.

Methods

Cell culture. hDP cells (from Promocell GmbH of Germany) were cultured in follicle dermal papilla cell growth medium (from Promocell GmbH of Germany) supplemented with 1% Pen-Strep. NHEKs (from Promocell GmbH of Germany) were cultured in keratinocyte growth medium (from Promocell GmbH of Germany) supplemented with 1% Pen-Strep (from Gibco of the United States of America).

Polyelectrolyte fiber drawing. In order to form the fiber matrix, fibers encapsulating the hDP cells and NHEKs were formed by the process of interfacial polyelectrolyte complexation (IPC) between sodium alginate and water soluble chitin (WSC).

To prepare the polycation precursor for hDP and NHEK cells, WSC (that was prepared from chitin from crab shell, obtained from Sigma-Aldrich of the United States of America) was dissolved in phosphate buffered saline (PBS) at concentrations ranging from 5 mg/ml to 20 mg/ml. 2—[μ]l of hDP and NHEK cell pellet solution (80 to 100 million cells/ml) was added to 8—[μ]l of polycation solution respectively and mixed thoroughly. A 10 mg/ml solution of sodium alginate (from Sigma-Aldrich of the United States of America) in deionized water was used as the polyanion.

As shown in FIG. 1a, 20—[μ]l of polyanion solution 2 was dispensed in between two adhesive modified pipette tips 4 while —[μ]l of polycation solution with hDP and NHEK (1,3) were dispensed on the outer opposite sides of the pipette tips 4. The solutions were allowed to come into contact with each other (as shown in FIG. 1b) and fibers were then drawn by an upward motion of the tip by a linear motor at a speed of 0.1 mm/s. Once the fibers reached a height of 5 cm, the linear motor was stopped and the base plate rotated at 5 rpm for 5 rounds to allow the fibers to fuse together. Subsequently, the linear motor was reactivated to continue the drawing process.

The fiber was drawn in a humidified chamber to protect the cells from drying. Subsequently, the cell laden fiber were subsequently rolled up by spooling on a two-pronged collection rod and fused to form a cell matrix construct by successive dipping into 5 mg/ml of WSC solution and 5 mg/ml of alginate solution. The resultant cell matrix construct was then placed in a culture medium (a 1:1 ratio of follicle dermal papilla cell growth medium and keratinocyte growth medium (both media were obtained from Promocell GmbH of Germany).

Example 1

Figure 2A:
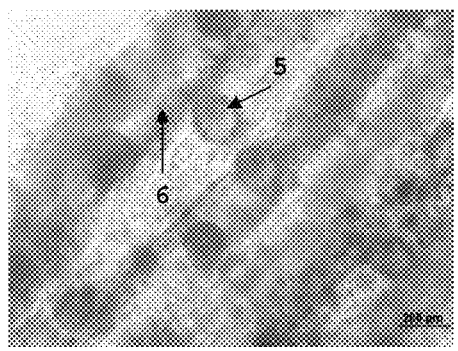
FIG. 2a is a bright field image showing the hair follicle like structure comprising hDP aggregates and layers of surrounding NHEK. The scale bar in the image is 200 µm.
Figure 2B:
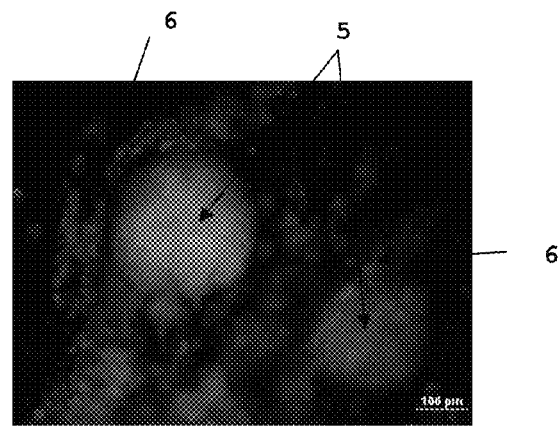
FIG. 2b is a fluorescence image of the same hair follicle like structure of FIG. 2a, but at higher magnification. The scale bar in the image is 100 µm. Images are taken at day 12 of culture.

The cell matrix construct obtained from the above IPC process was then cultured in the culture medium for 4 days to allow the formation of hair follicle-like structures. The assembly of the IPC fibers allowed the hDP cells and NHEKs to be brought into close proximity. The hDP cells aggregated to form spheroids of around 100 μm with the NHEKs surrounding these hDP aggregates forming structures resembling the hair follicle at day 12 of culture (see FIG. 2a in which reference numeral 5 represent the hDP spheroids and the reference numeral 6 represents the NHEKs). The hair follicle-like structures stained positive for versican which is an extracellular matrix secreted by anagen hDP cells (see FIG. 2b in which reference numeral 5 represent the hDP spheroids and the reference numeral 6 represents the NHEKs), indicating the ability to form hair follicles in vivo. As shown by FIG. 2a and FIG. 2b, the wrapping of the NHEKs around the hDP aggregates can be seen clearly.

Example 2

The cell matrix constructs were implanted subcutaneously in severe combined immunodeficiency (SCID) mice to ascertain the ability of these hair follicle-like structures to form hair follicles in vivo. FIG. 3a and FIG. 3b show images taken of hematoxylin and eosin stained sections of the explants. Hair follicles (shown by the arrows) were observed within the constructs from day 21 of implantation (see FIG. 3a), indicating that the cells in the hair follicle-like structures are viable and have the ability to form hair follicles in vivo. FIG. 3b is the same sample as FIG. 3a but taken at day 28 after implantation.

Example 3

In order to assess the suitability of the cell matrix constructs for hair drug testing, assays were carried out using a known hair growth promoter (hepatocyte growth factor, HGF) and inhibitor (transforming growth factor β2, TGFβ2). The growth factors were added to culture medium at a concentration of 10 ng/ml for HGF and 25 ng/ml for TGFβ2, The culture medium was changed every 2 days and the constructs were observed for 7 days.

From FIG. 4a, it can be seen that the cell matrix constructs with HGF had increased cell density, with formation of tubules and cysts as compared to the control shown in FIG. 4b in which the cell matrix constructs were grown in the absence of HGF.

From FIG. 4c, it can be seen that the cell matrix constructs with TGFβ2 had decreased cell density and the hDP aggregates formed were smaller compared to the control shown in FIG. 4d in which the cell matrix constructs were grown in the absence of TGFβ2.

In addition to qualitative observations, quantitative analysis was also carried out using these cell matrix constructs. The cell matrix constructs fixed at day 7 were stained for the proliferation marker Ki67, The hair follicle-like structures were then imaged using confocal microscopy (FIG. 5a to FIG. 5d) and an image analysis software, Image J, was used to quantify the area of Ki67 positive cells from the images taken. Subsequently, the percentage of proliferating cells was calculated by normalizing with the area of the aggregate (FIG. 6a and FIG. 6b).

Figure 5A:
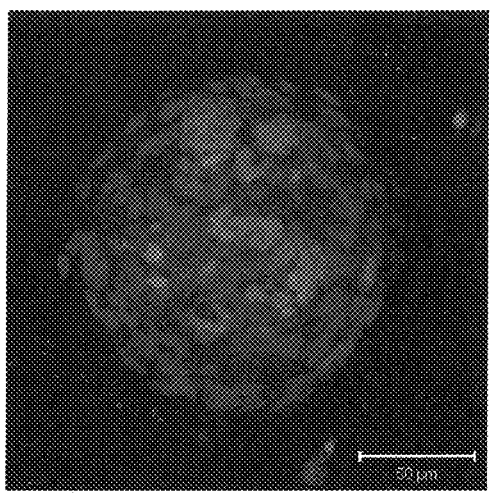
Figure 5B:
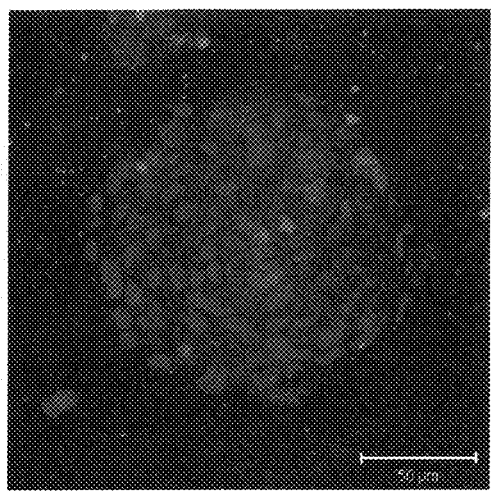
FIG. 5b is a micrograph image of the fibrous structure cultured without the hair growth promoter.
Figure 5C:
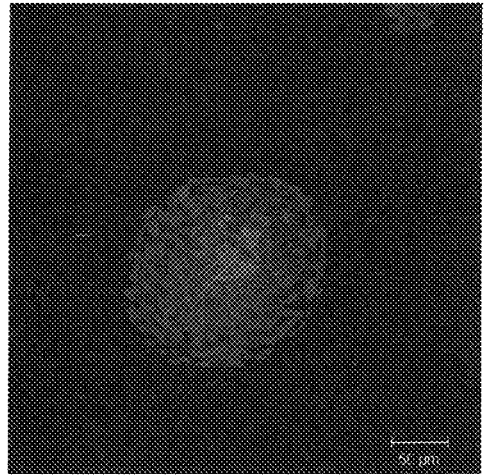
Figure 5D:
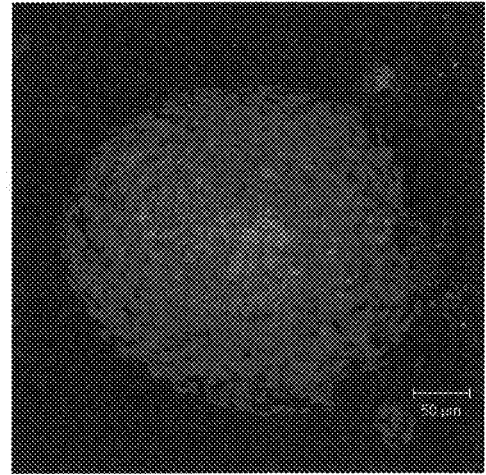
FIG. 5d is a micrograph image of the fibrous structure cultured without the transforming growth factor β2, The scale bar in all of the images is the same at 50 µm.
Figure 6A:
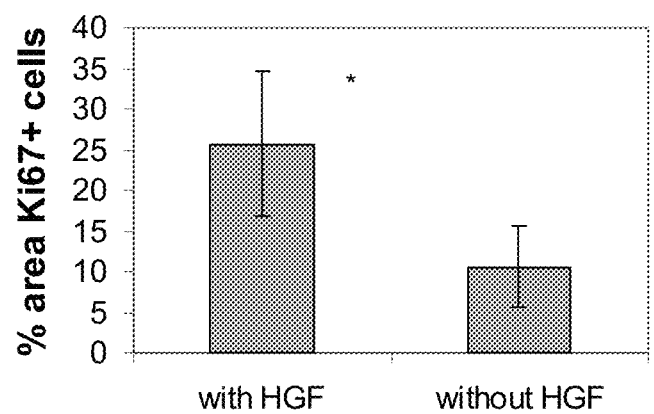
FIG. 6a is a graph showing the effects of hair growth promoter when used in the culture.
Figure 6B:
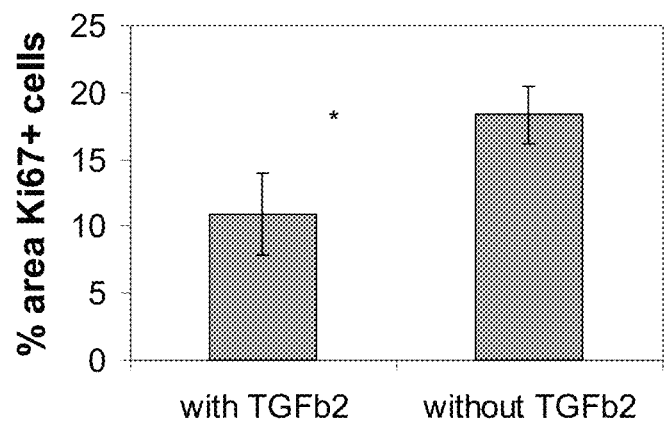
FIG. 6b is a graph showing the effects of transforming growth factor β2 when used in culture.
Figure 7A:
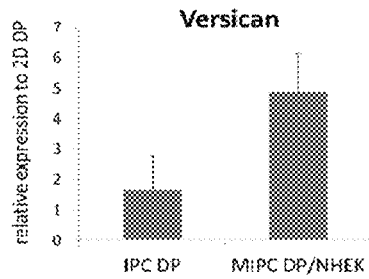
FIG. 7a is a graph showing the expression of versican between a construct that only has hDP cells and another construct that has both hDP cells and NHEKs.
Figure 7B:
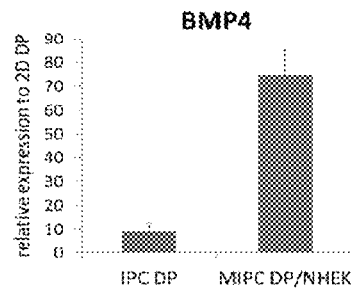
FIG. 7b is a graph showing the expression of bone morphogenetic protein 4 between a construct that only has hDP cells and another construct that has both hDP cells and NHEKs.
Figure 7C:
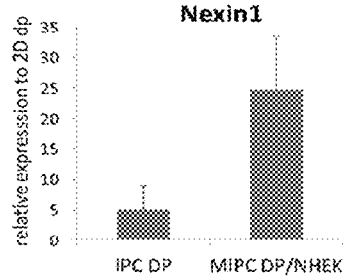
FIG. 7c is a graph showing the expression of nexin1 between a construct that only has hDP cells and another construct that has both hDP cells and NHEKs.
Figure 7D:
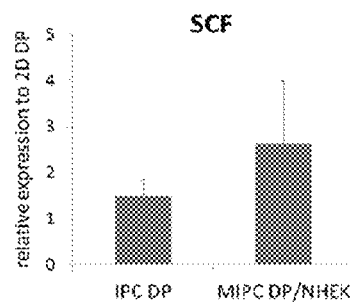
FIG. 7d is a graph showing the expression of stem cell factor between a construct that only has hDP cells and another construct that has both hDP cells and NHEKs.
Figure 7E:
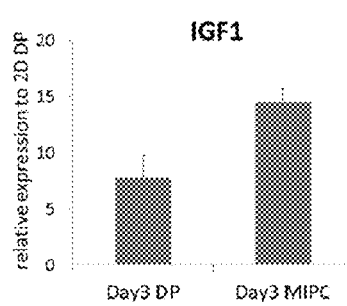
FIG. 7e is a graph showing the expression of insulin growth factor 1 between a construct that only has hDP cells and another construct that has both hDP cells and NHEKs. Gene expression levels of all the constructs are shown relative to the expression of hDP cells cultures on 2D plates.

The results obtained showed that HGF increases the percentage of proliferating cells (when comparing FIG. 5a to the control of FIG. 5b) while TGFβ2 decreases the percentage of proliferating cells (when comparing FIG. 5c to the control of FIG. 5d). This is also seen in the graphs of FIG. 6a and FIG. 6b for the HGF and TGFβ2 assays respectively. (the * in FIG. 6a and FIG. 6b denotes significant difference between the two groups, p<0.05 (student's t test).

This above findings are in agreement with the known promoting and inhibiting effect of HGF and TGFβ2 respectively. The assays carried out indicated that the hair follicle-like structures in the IPC cell matrix constructs are suitable for testing the hair growth promoting/inhibiting effect of drugs.

Example 4

Real-time polymerase chain reaction (PCR) was carried out to analyse the gene expression of the hDP structures assembled in the fiber matrix. Samples analysed include a cell matrix construct with a co-culture of hDP cells and NHEKs (labeled as MIPC DP/NHEK) and a cell matrix construct with only hDP cells (labeled as IPC DP). These samples were compared to a control sample of hDP cells cultured on tissue culture plates. The samples were sacrificed after 4 days of culture to allow the organization and formation of hDP structures.

Total RNA was extracted from the cell matrix constructs using Trizol reagent (from Invitrogen of the United States of America) according to the manufacturer's protocol. RNA samples were treated with DNAse I (from Invitrogen of the United States of America) to remove contaminating genomic DNA, and cDNA was subsequently synthesized using SuperScript III Reverse Transcriptase and Oligo (dT)18 primers (from Invitrogen of the United States of America) according to manufacturer's instructions. RT-PCR was carried out using Power SYBR Green PCR Master Mix (from Applied Biosystems of the United States of America). Genes which have been found to be expressed in the native hair follicle (particularly in the hDP) during the hair cycle such as versican, bone morphogenetic protein 4 (bmp4), nexin1, stem cell factor (scf) and insulin growth factor 1 (IGF1) were investigated and measured. Primer sequences used are as follows: Versican: CCAGCAAGCACAAAATTTCA [Seq. ID #1] and TGCACTGGATCTGTTTCTTCA [Seq. ID #2]; BMP4: TCCACAGCACTGGTCTTGAG [Seq. ID #3] and GGGATGTTCTCCAGATGTTCTT [Seq. ID #4]; Nexin1: GCGTAAATGGAGTTGGTAAA [Seq. ID #5] and GTCTATGGTCTTGGTGCTGA [Seq. ID #6]; IGF1: CCTCCTCGCATCTCTTCTACCTG [Seq. ID #7] and CTGCTGGAGCCATACCCTGTG [Seq. ID #8]; SCF: CCATTGATGCCTTCAAGGAC [Seq. ID #9] and GGCTGTCTCTTCTTCCAGTA [Seq. ID #10].

The above genes were selected for analysis because they are involved in the signaling exchanges during epithelial mesenchymal interactions. The epithelial mesenchymal interactions between the epidermal keratinocytes and the dermal papillae control the development and cycling of hair follicles. Therefore, it is important to allow interaction between keratinocytes and dermal papilla to develop effective hair follicle models. The above genes are expressed by the dermal papilla. Versican is a proteoglycan which has been reported to be expressed by the dermal papilla of anagen stage fiber-producing hair follicles. In addition, dermal papilla cells positive for versican are able to induce hair formation when implanted in vivo. IGF1 and nexin1 are expressed in the dermal papilla during anagen stage but not the catagen stage, suggesting that these molecules play a part in controlling the hair cycle.

The results from the above analysis are shown in FIG. 7a to FIG. 7e.

From the above gene expression study, since the gene expression levels presented in the graphs were normalized to data from 2D controls, it was found that expression of these genes were higher for the hDP aggregates in the IPC DP sample as compared to hDP cells on 2D culture plates. This may indicate that formation of three-dimensional hDP aggregates improves the maintenance of their native characteristics. The advantage of forming hDP aggregates is that the hDP spheres have better hair inductive ability in vivo as compared to dissociated hDP cells. More importantly, gene expression was even higher for the MIPC DP/NHEK sample. Formation of follicular hDP structures through multi-IPC assembly allows interaction between the hDP aggregates and NHEK, and genes up regulated suggest presence of signaling network which is characteristic of epithelial mesenchymal interactions in the native hair follicle.

Hence, it can be seen that the presence of at least two types of hair follicle cells (in this case, hDP cells and NHEKs) resulted in a hair follicle like structure with some biological characteristics of an actual hair follicle.

Applications

The fibrous structure may be used as a testing platform to determine the efficacy and suitability of a drug for hair treatment.

The fibrous structure may be incorporated into a skin patch or implanted into an organism to promote hair growth.

The fibrous structure may be monitored easily either by the naked eye or under a suitable microscopy technique for qualitative and quantitative observations. This can be possible due to the transparent nature of the polyelectrolyte fibers. As such, any changes to the hair follicle cells due to a change in the media for fresh addition of drugs to be tested can be carried out easily.

The fibrous structure can be fixed and stained easily if required for analysis.

A plurality of fibrous structure can be combined together to form a bigger test platform so as to provide a larger population for data collection.

The method to form the fibrous structure may be carried out with ease using the IPC fiber assembly technique. Since the hair follicle cells are capable of self-assembling, it is not necessary for a user to intervene, leading to lesser number of steps involved.

The method may be relatively fast, allowing for higher throughput of the cell laden constructs which is important for drug assays.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

---

The invention claimed is:

1. A fibrous structure comprising an assembly of hair follicle cells within a fibrous matrix, wherein the fibrous matrix is made up of a plurality of polyionic fibers, and wherein said assembly comprises human dermal papilla cells in the form of spheroids, wherein said spheroids are at least partially surrounded by normal human epidermal keratinocytes.

2. The fibrous structure of claim 1, wherein the diameter of the spheroids is in the range of 80 μm to 120 μm.

3. The fibrous structure of claim 1, wherein said polyionic fibers comprise at least one polycationic polymer and at least one polyanionic polymer, said polycationic polymer and polyanionic polymer being biocompatible or biodegradable.

4. A method of forming a fibrous structure comprising the step of providing an assembly of hair follicle cells within a fibrous matrix, said fibrous matrix comprising a plurality of polyionic fibers and wherein said assembly of hair follicles comprises human dermal papilla cells in the form of spheroids, wherein said spheroids are at least partially surrounded by normal human epidermal keratinocytes.

5. The method of claim 4, wherein said providing step comprises the step of drawing a fiber from the interface between a polyanionic polymer solution and a polycationic polymer solution to form said fibrous matrix, wherein said hair follicle cells are present in at least one of said polycationic polymer solution and polyanionic polymer solution.

6. The method of claim 4, wherein two or more types of hair follicle cells are present in at least one of said polycationic polymer solution and said polyanionic polymer solution.

7. The method of claim 4, wherein two or more types of hair follicle cells are present in two or more polycationic polymer solutions.

8. The method of claim 7, wherein when two polycationic polymer solutions are used, human dermal papilla cells are present in one polycationic polymer solution and normal human epidermal keratinocytes are present in the other polycationic polymer solution.

9. The method of claim 4, wherein two or more types of hair follicle cells are present in two or more polyanionic polymer solutions.

10. The method of claim 9, wherein when two polyanionic polymer solutions are used, human dermal papilla cells are present in one polyanionic polymer solution and normal human epidermal keratinocytes are present in the other polyanionic polymer solution.

11. The method of claim 6, wherein the concentration of said hair follicle cells in at least one of said polycationic polymer solution and said polyanionic polymer solution is in the range of 70 to 110 million cells/ml.

12. The method of claim 4, comprising the step of fusing said plurality of polyionic fibers to thereby form said fibrous matrix.

13. The method of claim 12, wherein said fusing step comprises the step of rotating a base plate supporting the plurality of formed fibers.

14. The method of claim 13, comprising the step of treating the fibrous matrix in a polycationic polymer solution followed by a polyanionic polymer solution.

* * * * *